Figure 1A:
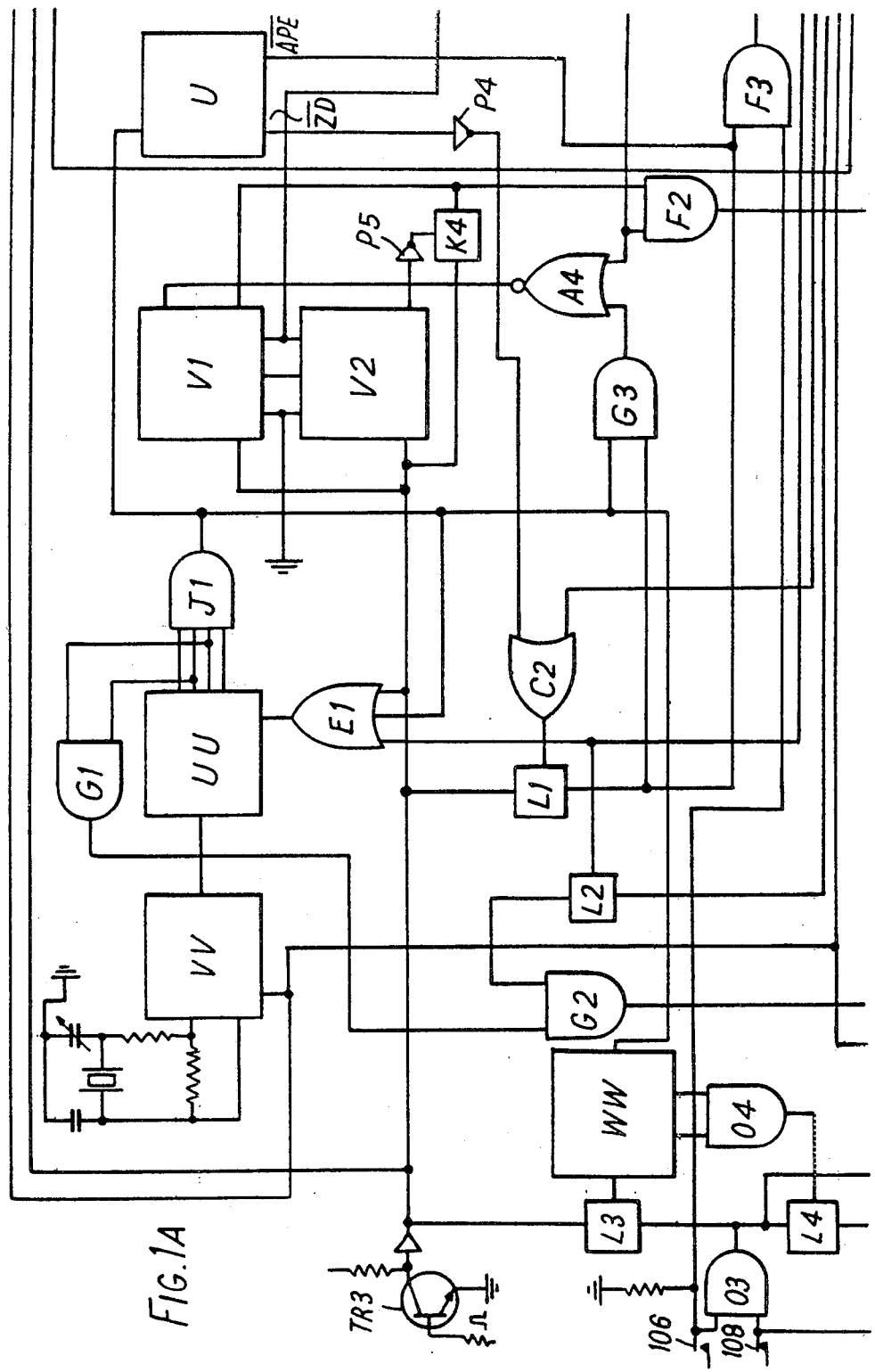

United States Patent [19]

Wolff et al.

[11] 4,396,020

[45] Aug. 2, 1983

[54] MEASUREMENT OF BASAL BODY TEMPERATURE

[75] Inventors: Heinz S. Wolff, London, England; Robert M. Abrams, Gainesville, Fla.; John P. Royston; Simon J. E. Humphrey, both of London, England

[73] Assignee: National Research Development Corporation, London, England

[21] Appl. No.: 216,895

[22] Filed: Dec. 16, 1980

[30] Foreign Application Priority Data

Dec. 21, 1979 [GB] United Kingdom ................ 7944063

[51] Int. Cl.³ .............................................. A61B 5/00
[52] U.S. Cl. .................................... 128/738; 128/736; 374/102
[58] Field of Search ............................. 128/736, 738; 73/362 AR; 331/66; 364/417, 557; 374/100–103, 107, 108

[56] References Cited

U.S. PATENT DOCUMENTS 3,822,598  7/1974  Brothers et al. ............... 73/362 AR
4,031,365  6/1977  Raggiotti et al. ............... 128/736 X
4,151,831  5/1979  Lester .............................. 128/738 X Primary Examiner—Lee S. Cohen
Assistant Examiner—Angela D. Sykes
Attorney, Agent, or Firm—Flynn, Thiel, Boutell & Tanis

[57] ABSTRACT

Temperature readings from a thermistor 16 can be recorded in a counter 20 by means of a self-balancing bridge 17 when gate 15 is open for the same four hours of each day. Clock 10 is set to initiate the four hour period at say 06.00 hrs. so that the body temperature measurement is taken after waking but before rising. Measurements for the first three days of the menstrual cycle are rejected (19) and for the next eight days are accummulated in a store 22. These measurements are subject to a diurnal correction 21 to reduce them to the temperature at the beginning of the 4 hour period. The mean of eight readings is determined (23) and subsequent readings compared (24) with the mean. A Cusum statistical test is then applied to determine the beginning of the infertile period signalled by a rise in body temperature and produce a corresponding display 27.

12 Claims, 6 Drawing Figures

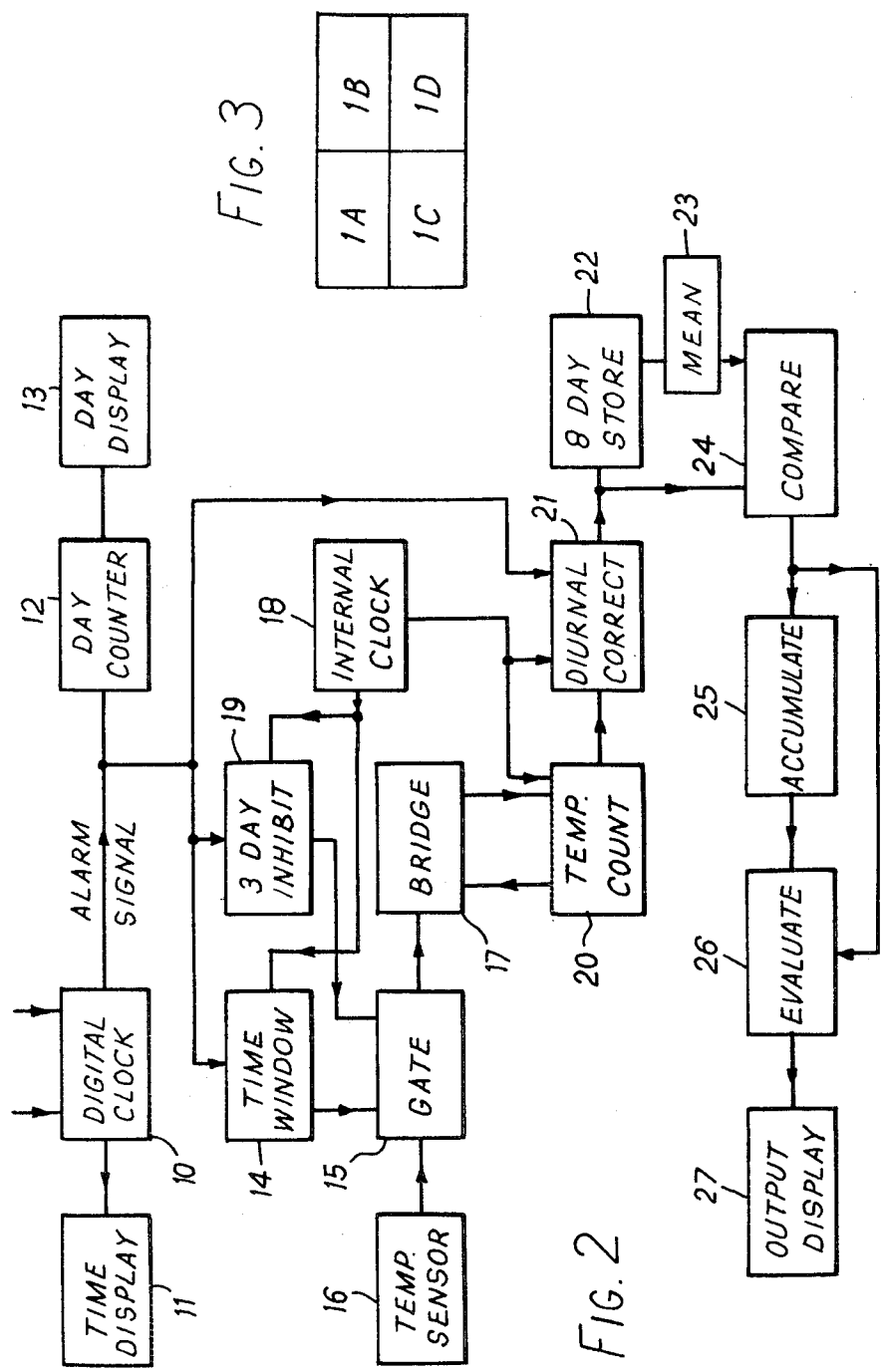

MEASUREMENT OF BASAL BODY TEMPERATURE

The present invention relates to the measurement of basal body temperature for the purpose of natural family planning.

This method of family planning is based on the fact that an upward shift in a woman's basal body temperature to an established higher level indicates that sufficient time has elapsed from the occurrence of ovulation for the commencement of a period of infertility. The basal body temperature is obtained by taking a temperature measurement at a standard time which should be just after waking and before rising. As at present used the method involves taking temperature measurements with a mercury-in-glass thermometer, recording the daily measurements in graphical form, and interpreting the graph by some simple algorithm in order to identify the occurrence of the significant upward shift in temperature.

The present invention seeks to provide an instrument for making and interpreting the temperature measurements which will be so simple to use that it will enable the method to be used by women who are daunted by the complexity of the present procedure and unable to carry it out reliably.

In accordance with the present invention there is provided an electrical instrument for basal body temperature measurement comprising a clock, an entry circuit for electrical temperature signals from a temperature sensor, the entry circuit being so controlled by the clock that entry of a temperature signal is permitted only during a predetermined time period of each day, a store for accumulating a number of entered daily temperature signals, means for processing the accumulated signals to establish a mean temperature level, means for comparing subsequent entered temperature signals with the mean temperature level and calculating when a significant rise in temperature has taken place, and an indicator for displaying the fact of occurrence of the significant temperature rise.

Conveniently such an instrument is used with a thermistor temperature transducer which is placed under the user's tongue. In a preferred embodiment the mode of use is as follows.

(i) The first temperature measurement is made on the 1st day after the onset of menstrual bleeding. The user inserts the transducer into the mouth and presses the "enter" button. If the sequence is initiated within a 4 hour time window (say between 6.00 am and 10.00 am) which has been preset into the machine, the user is answered by a bleep. If outside the window no measurement can be entered. The transducer is then retained in the mouth until a second bleep sounds (say after 3 mins).

(ii) For the first three days the temperature readings are ignored by the instrument and for the next eight readings they are accumulated, the average of the eight temperatures being determined. If days are missed or if readings are rejected as invalid because they are outside a set range of temperature (35.8° to 37.6° C.) the instrument will carry on, until it has accumulated eight valid readings.

(iii) After the eighth valid reading, the instrument performs the following calculations each day. B is the mean temperature derived from the first eight readings, $T_n$ is the temperature measured on the current day, K is a pre-programmed constant related to the minimum BBT rise considered to be physiologically significant and H is the decision level, also constant.

1st Calculation: $E_n = T_n - (B+K)$, where $n = 1, 2, 3 \ldots$

2nd Calculation: $S_n = S_{n-1} + E_n$. ($S_o$ is taken to equal zero)

3rd Calculation: If $S_n$ is less than zero, $S_n$ is set equal to zero; otherwise no change.

4th Calculation: $D_n = H - S_n$.

If $D_n \leq 0$ for the current day and if $E_n \geq 0$ for the current day and also for the past two days, then the instrument latches in that state and displays an indication that the "infertile period" has started.

(iv) The user may then stop taking daily temperatures until the start of the next menstrual period.

The user resets the instrument at the commencement of the next menstrual cycle by pressing the "enter" and "read" buttons simultaneously.

The calculations made constitute a modified Cusum statistical test to determine when an upward temperature shift is significant. The details of the test and the magnitude of K and H may be changed as further records are accumulated and analysed. In essence the instrument makes whatever statistical check is necessary to establish that the significant temperature change has occurred.

To reduce the scatter of the temperature readings and thus improve the reliability of the Cusum test, the instrument makes an automatic correction to each temperature reading according to the time of measurement. This is possible because the rate of rise of postmenstrual temperature of women before waking has been found to be close to 0.1° C./hr. and by reducing the measured temperature in accordance with this rate of rise all the temperatures are adjusted to a value close to that which would have been obtained if the reading had always been taken at the beginning of the time window.

The instrument incorporates a digital clock which provides a normal time display for the user and also gives an alarm signal which sets the temperature measuring and evaluation circuits at the beginning of the four hour period each day. The time window setting is not accessible to the user of the instrument but the user can adjust the time on the clock in case of a change of time zone and this automatically adjusts the 4-hour window.

An additional counter and display are reset to zero when the instrument is re-set at the beginning of a cycle and increments by one at the start of each 4-hour window, thus counting the day of the cycle regardless of whether a temperature measurement is taken.

The instrument could be constructed using a microprocessor chip, memory devices, a clock oscillator, and a small number of peripheral chips. The present embodiment, however, uses CMOS counters and logic blocks in a hardwired configuration together with a quartz crystal clock.

Figure 1B:
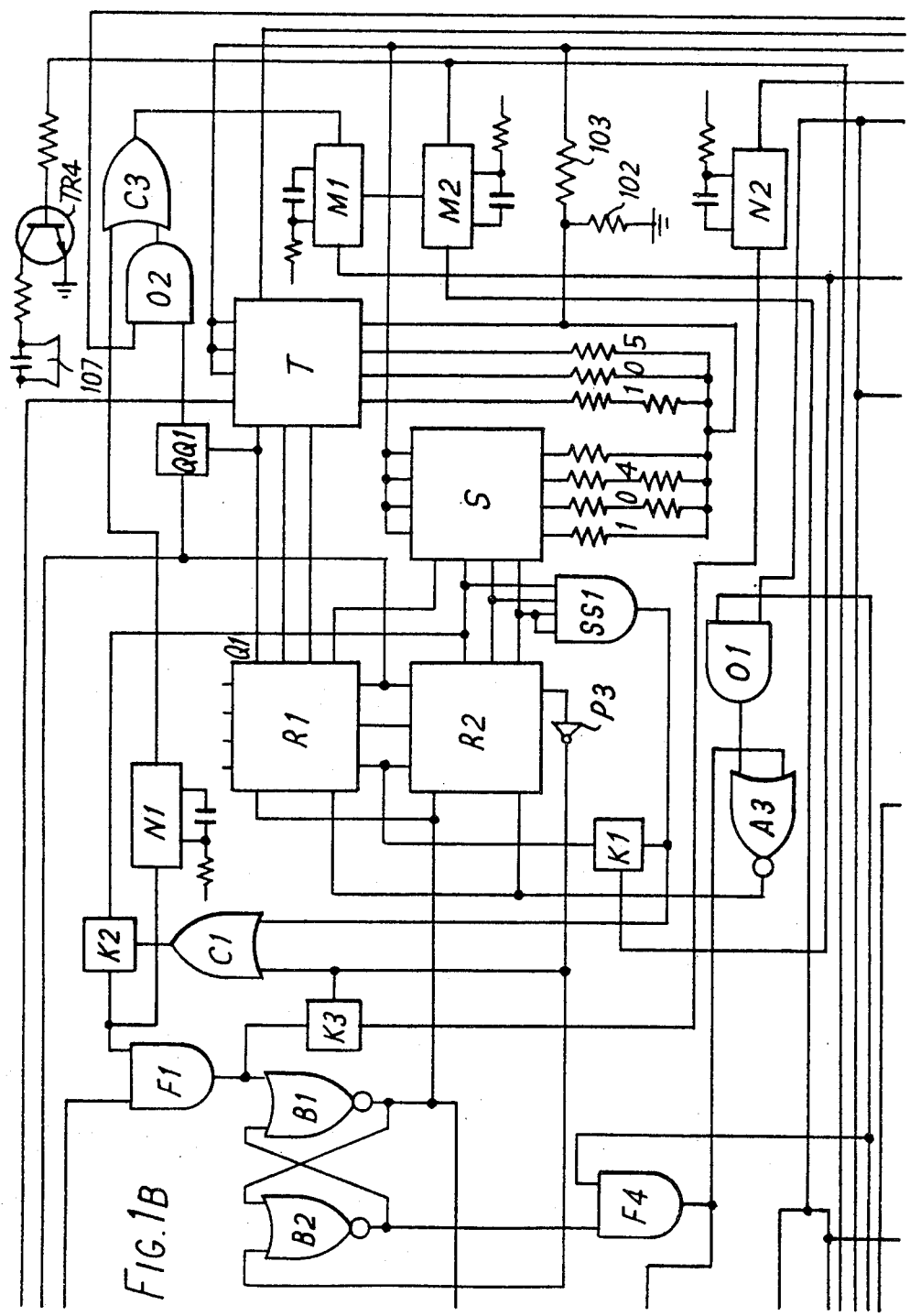
Figure 1C:
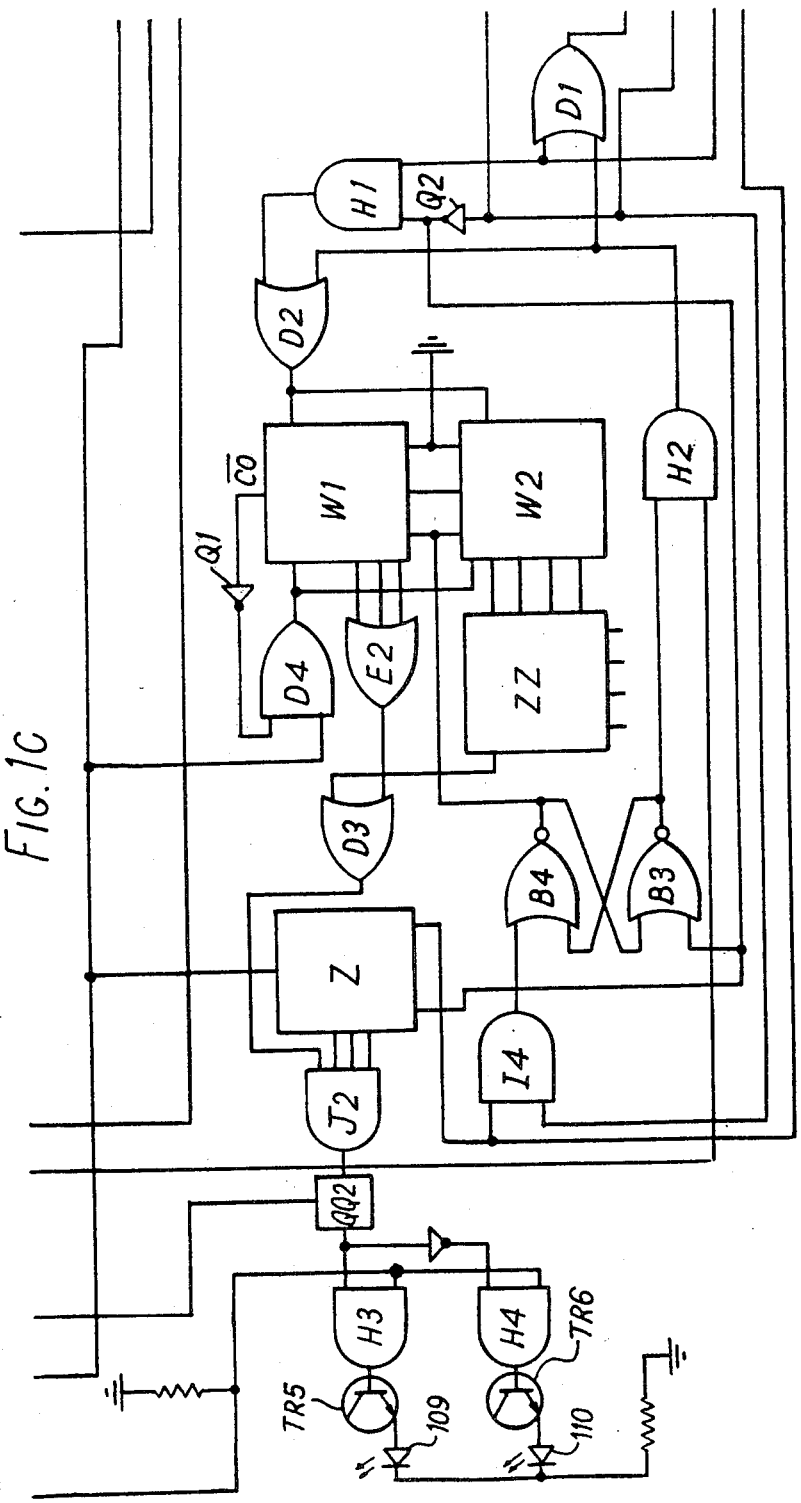
Figure 1D:
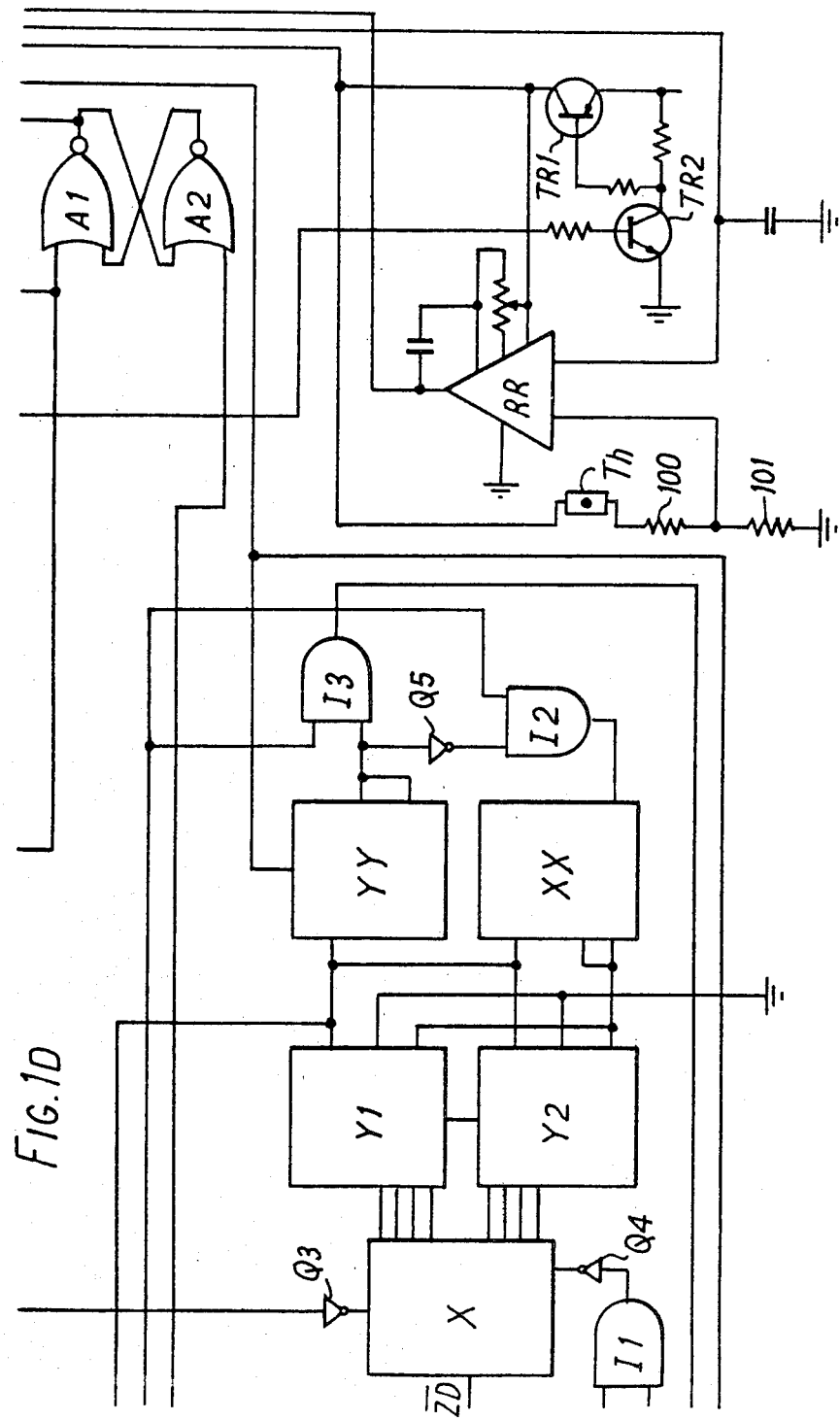

By way of example this embodiment will now be described in detail with reference to the accompanying drawings, in which:

FIGS. 1A, 1B, 1C and 1D, when assembled as shown in FIG. 3, show the circuit logic of the instrument, omitting the digital clock and the day counter, FIG. 2 is a schematic diagram of the operations performed by the instrument.

Referring first to FIG. 2, the instrument incorporates a digital clock 10 providing a conventional time display 11. The time recorded by the clock can be set by the user but the time of commencement of the four hour window can only be set inside the instrument and does not thereafter need changing. The clock 10 generates an alarm signal each day at the beginning of the four hour window. This is passed to a delay counter 12 with manual reset, which controls a day display 13 showing the day of the cycle.

The alarm signal from the clock 10 is also applied to the measurement and evaluation circuits which are shown in detail in FIGS. 1A to 1D. As shown in outline in FIG. 2 the alarm signal triggers a time window circuit 14 which controls a gate 15 through which temperature signals from a temperature sensor 16 pass to a self-balancing bridge circuit 17. The time window circuit 14 measures the 4 hour window within which temperature readings can be taken and for this purpose is supplied with timing pulses from an internal clock 18. These timing pulses are also fed to a 3-day inhibit circuit 19 which holds the gate 15 closed until the fourth day to prevent entry of temperature readings in the first three days.

The bridge 17 is controlled by a temperature counter 20 which records the value at which the bridge is balanced and passes this temperature measurement by way of a diurnal correction circuit 21 to the evaluation circuits. The correction circuit 21 is triggered at the beginning of each 4 hour window by the alarm signal and corrects each measured temperature according to the time during the window at which the measurement was taken.

The first eight temperature readings (after rejection of readings taken on the first three days) are passed to an 8 day store 22 and the mean 23 of these readings is passed to a comparator 24 for comparison with subsequent readings. The differences ascertained by the comparator 24 are passed to an accumulator 25 and the accumulated excess over the mean is passed to an evaluation circuit 26. The evaluation circuit also receives the individual outputs from the comparator 24 and requires three of these in succession to be positive and the accumulated excess to be above the significance level before switching an output display 27 to indicate the commencement of an infertile period.

The temperature measurement is effected by a self-balancing bridge. A thermistor Th (FIG. 1D) is connected in series with a linearising resistor 100 in one arm of the bridge. A second arm is a resistor 101 and a third arm is a resistor 102 (FIG. 1B) equal in value to resistor 101 and preferably also approximately equal to the combined value of resistor 100 and thermistor Th for maximum sensitivity. The fourth, balancing, arm of the bridge comprises a resistor 103 in parallel with which resistor 104 and resistor 105 can be selectively connected by switches S and T. The null point of the bridge is detected by an amplifier RR connected as a comparator. Power is supplied to the bridge and amplifier RR through transistor TR1 in response to a control signal at the base of transistor TR2.

The switches S and T, in the form of analogue gates, are controlled by counters R1+R2. At the beginning of a measurement these have been re-set and they begin to count up when clock pulses from VV are supplied through 01 and A3. As the counters are incremented the resistors 104 and 105 are connected in parallel with resistor 103 according to a binary sequence until the bridge is balanced. The values of the resistors are calculated such that each step in the sequence corresponds to the same change of temperature of the thermistor Th.

When balance is reached the output of the comparator RR changes over and triggers monostable M1 through 02 and C3. The output of M1 resets latch A1/A2 which then switches off the transistors TR2 and TR1 and closes gate 01, stopping the supply of clock pulses to the counters R1+R2.

The gate 02 is controlled by the output of latch QQ1 so that a high pulse from RR can only be transmitted to M1 if QQ1 is high. At the start of the measurement QQ1 is low but is set high when output Q1 of counter R1 goes high. This prevents a pulse from RR, occurring when power is switched on, instantly resetting A1/A2.

The counters R1+R2 thus hold the measured temperature value, which will only be accepted as valid if in a predetermined temperature range. Gate F1 is only opened by setting of K2 when a minimum temperature count is reached in R2. If the temperature count has gone beyond an upper limit the decoder SS1 sets latch K1 to reset counters R1+R2 and closes gate F1 by resetting latch K2 via C1. This prevents the temperature reading being passed to the evaluating circuits in the manner now to be described.

With F1 open the output of M1, which terminates the measurement, also sets B1 through F1. This in turn opens F4 and allows clock pulses from VV to reach R1+R2 through F4 and A3. These decrement the counter and when the counter reaches zero, an output through P3 resets B2, closing F4. At the same time K2 and K3 are reset. K2 closes F1 and triggers monostable N1, thereby triggering M1 through C3 and resetting A1 and K1 to complete the temperature measurement. K3 was set when B1 was set by the output of M1. The setting of K3 indicates a valid temperature reading and triggers N2 to pass a pulse to counter YY.

As the counters R1+R2 are counted down the clock pulses passing through F4 reach one input of gate F2 whose output is applied via I2 to a counter XX which records the valid temperature readings. However, by delaying the opening of gate F2 a correction is made to allow for the time at which the temperature reading was taken. This involves the timing of the whole apparatus and the equipment for maintaining the correct timing will now be described.

A conventional clock with a digital display is provided in the apparatus and controls the commencement of the period within which temperature measurements can be taken. Thus if the clock is adjusted on passing into a different time zone the alarm signal from the clock controlling the temperature measurement circuits automatically occurs at the same hour. This alarm signal, the hour of which is preset within the equipment, is applied to the circuit of FIG. 1A via a transistor TR3. The occurrence of the alarm signal marks the beginning of a four hour measurement period and the alarm signal is effective to re-set counters UU, V1+V2, and R1+R2 and latches K4 and QQ1 and L3 and set latch L1. A crystal-controlled oscillator VV provides fast clock pulses at 1024 Hz to F4 and O1 and slow timing pulses at 2 Hz to counter UU. The gate J1 connected to the output of UU provides 12 minute pulses to counters U and WW. Counter U controls the four hour measurement period by counting twenty of the 12 minute pulses when enabled by output from L1 applied to APE, after which the output ZD, inverted by P4, resets latch L1, thereby closing gate F3 to prevent entry of any further measurement.

To make a temperature reading, the user places the temperature sensor in position and presses an enter button to operate a switch 106 and cause the output of F3 to go high. This resets UU and sets L2 to open gate G2. A gate G1 connected to the output of UU provides a pulse after a delay of 3 minutes 12 seconds. This pulse is passed by gate G2 to set A2 high and commence a temperature measurement. The delay allows the thermistor to reach body temperature after being placed in position. The output of A1 resets L2 and closes gate G2 to stop any further pulses from G1.

The counter UU is reset via E1 by the alarm signal at the beginning of the 4 hour period, by the output of J1 every twelve minutes, and by the output of F3 when the enter button is pressed. Also when the enter button is pressed the output of F3 triggers monostable M2 whose output generates an audible bleep signal by means of transistor TR4 and microphone 107. The output from M2 also resets L1 via C2, to prevent further entries during the 4 hour window. M2 is also triggered to produce a bleep when M1 is triggered as a result of C3 going high. Thus the first bleep when the entry button is pressed is followed by a second bleep when the measurement is taken or when the upper limit of temperature is reached by the counters R1+R2.

At the beginning of every 4 hour time window for the entry of temperature measurements the counters V1+V2 are reset to zero by the alarm signal from TR3. Gate G3 is held open by latch L1 and allows clock pulses from J1 to pass to A4 and count up in the counters V1+V2 from the beginning of the four hour window. When latch L1 is reset as a result of pressing of the entry button G3 is closed and the count stopped. When the counters R1+R2 are being counted down by the fast clock pulses from F4 these initially also pass via A4 to counters V1+V2, where they count down a recorded count which is representative of the time during the 4 hour window at which the measurement is taken. The measured temperature is reduced by 0.1° C. per hour to adjust the temperature to a value close to that which would have been obtained at the beginning of the 4 hour period. When the diurnal correction counters V1+V2 have been counted down to zero a signal through inverter P5 sets K4 which inhibits any further count by the counters V1+V2 and opens the gate F2. Thus the remaining pulses during the count-down of R1+R2 are sent as corrected temperature readings to counter XX (FIG. 1D) via gate I2.

The enter button switch 106 supplies one input of a gate 03. The other input is from a read button switch 108. The pressing of the read and enter buttons provides a reset signal at the output of 03. This occurs on day one of a new cycle of temperature measurements and, in particular, resets latch QQ2. A counter WW supplied with 12 minute clock pulses from J1 is initially held reset at zero by a reset pulse from 03. On day 2 the alarm signal at the beginning of the 4 hour window resets latch L3 and starts the counter WW. The output of gate 04 goes high after a further two days and resets L4 at the beginning of the time window on day 4. The output of L4, which has been high for 3 days and has held a shift register Z and counters W1+W2, Y1+Y2, YY and XX reset during that period, now goes low and allows readings taken from day 4 onwards to be evaluated.

The mean temperature B is determined by taking the mean of the first eight temperature readings, starting with the reading on day 4. For this purpose the corrected temperature readings received by XX are fed from a divide-by-eight terminal to the counters Y1+Y2 which carry a preset count of 5. This represents the constant K with a value of 0.1° C. related to the minimum BBT rise considered to be physiologically significant. The counter Y receives a pulse from N2 for every valid temperature reading. When it has counted eight readings its output inhibits any further count, closes the gate I2 and opens a gate I3. Subsequent readings therefore pass from I3 to D1 and thence via I1 and Q4 to counter X. Counter X is preset to (B+K), the value in the counters Y, by an enter pulse from F3 received via Q3. The new reading counts down from this preset value. When the counter X reaches zero, output ZD goes low and this signal closes I1 and, inverted by Q2, opens H1 so that any remaining pulses pass via H1 and D2 to counter W1+W2 which is incremented by the excess of this reading over (B+K). Output ZD going low also closes I4 and the inverted signal through Q2 resets B3 and is applied to pin 15 of shift register Z.

If counter X does not reach zero when a reading is taken, the control pulse from N2 opens gate H2 by setting B4 through I4. Fast clock pulses from VV are then passed by H2 to D1 and D2 to count down counters X and W1+W2. When X reaches zero the output ZD goes low (closing I1 and I4) and the inverted signal through Q2 closes B3, closing H2 and setting counters W1+W2 to count up. The counters W1+W2 are prevented from going below zero by the low output from CO passed by Q1 and D4 to hold the counter reset at zero.

When X has reached zero before the control pulse from N2 is applied to the shift register Z, the pin 15 has been set high and the control pulse clocks in a "1" to the shift register, indicating a temperature reading exceeding B+K. If the control pulse arrives before X has reached zero, a "0" is recorded by the shift register Z. When three '1's have been recorded ($E_n > 0$) for successive readings and when the Cusum exceeds the significance level ($D_n \leq 0$) the output of J2 goes high and sets latch QQ2. This then opens gate H3 and closes gate H4 so that pressing the read button to close switch 108 illuminates a green light-emitting diode 109 via transistor TR5 instead of a red diode 110 via transistor TR6.

The significance level of 13 representing 0.25° C. is set in counter ZZ and is compared with the Cusum accumulated in counters W1+W2. When the Cusum exceeds the significance level the output of D3 goes high either by a signal from ZZ or by a higher count recorded in W1 and reaching D3 via E2. If, in addition, the shift register Z has recorded three successive high readings, J2 sets the latch QQ2 as described above.

We claim:

1. An electrical instrument for basal body temperature measurement comprising a clock, an entry circuit for electrical temperature signals from a temperature sensor, means so controlling the entry circuit by the clock that entry of a temperature signal is permitted only during a predetermined time period of each day, means connected to the entry circuit for reducing each entered temperature signal by an amount proportional to the time elapsed between the beginning of the predetermined time period and the time of entry of the temperature signal, a store connected to the reducing means for accumulating a number of entered daily temperature signals after reduction, means for processing the accumulated signals to establish a mean temperature level, means for comparing subsequent entered temperature signals with the mean temperature level and calculating when a significant rise in temperature of predetermined significance has taken place, and a first indicator means for displaying the fact of occurrence of the significant temperature rise.

2. An instrument as claimed in claim 1 wherein the entry circuit includes an entry switch operable by the user to initiate entry of a temperature signal.

3. An instrument as claimed in claim 2 including delay means coupled to said entry switch to delay entry of the temperature signal until the temperature sensor has attained body temperature.

4. An instrument as claimed in claim 3 including a section indicator means connected to the clock for indicating to the user when a temperature signal is entered.

5. An instrument as claimed in claim 1 including validating means permitting only temperature signals within a predetermined temperature range to be entered into the entry circuit.

6. An instrument as claimed in claim 1 including means for preventing the first few temperature signals from reaching the store.

7. An instrument as claimed in claim 1 wherein said calculating means includes means for recording the algebraic sum of the differences between successive temperature signals and the mean temperature level, and means for comparing the said algebraic sum with a predetermined significance level.

8. An instrument as claimed in claim 7 including means for recording when the temperature signal exceeds the mean temperature level, said excess recording means being activated only when the significance level is exceeded and three successive temperature signals have exceeded the mean temperature level.

9. An instrument as claimed in claim 7 in which said means for comparing the temperature signals with the mean temperature level has means for reducing each temperature signal before comparison by a constant amount related to a minimum temperature rise which is physiologically significant.

10. An instrument as claimed in claim 1 in which the entry circuit is connected to a self-balancing bridge circuit for determining the resistance of a thermistor temperature sensor.

11. An instrument as claimed in claim 1 in which the clock includes means for generating an alarm signal at a specified time each day and the instrument includes timing circuits triggered by the alarm signal from the clock for controlling the entry circuit.

12. An instrument as claimed in claim 1 including a day counter connected to the clock for recording and displaying the day of the cycle.

* * * * *

UNITED STATES PATENT AND TRADEMARK OFFICE
CERTIFICATE OF CORRECTION

PATENT NO. : 4 396 020
DATED : August 2, 1983
INVENTOR(S) : Heinz S. Wolff et al It is certified that error appears in the above—identified patent and that said Letters Patent is hereby corrected as shown below:

Column 7, line 12; change "section" to ---second---.

Signed and Sealed this

Eighteenth Day of October 1983

[SEAL]

Attest:

GERALD J. MOSSINGHOFF

Attesting Officer

Commissioner of Patents and Trademarks